United States Patent [19]

Nagata et al.

[11] Patent Number: 4,804,783

[45] Date of Patent: Feb. 14, 1989

[54] PROCESS FOR PRODUCING DIPHENYLAMINES OR N,N'-DIPHENYL-PHENYLENEDIAMINES

[75] Inventors: Teruyuki Nagata; Akihiro Tamaki; Nobuyuki Kajimoto; Masaru Wada, all of Ohmuta, Japan

[73] Assignee: Mitsui Toatsu Chemicals, Inc., Tokyo, Japan

[21] Appl. No.: 80,440

[22] Filed: Jul. 31, 1987

Related U.S. Application Data

[60] Continuation of Ser. No. 903,427, Sep. 4, 1986, which is a division of Ser. No. 710,662, Mar. 12, 1985, abandoned.

[30] Foreign Application Priority Data

Mar. 14, 1984 [JP] Japan .................. 59-47119
Mar. 27, 1984 [JP] Japan .................. 59-57339
Jul. 6, 1984 [JP] Japan .................. 59-138894

[51] Int. Cl.$^4$ .................................. C07C 85/06
[52] U.S. Cl. ........................... 564/402; 564/397; 564/398; 564/433; 564/434; 564/435; 560/48; 562/457; 558/418
[58] Field of Search ............... 564/397, 398, 402, 433, 564/434, 435; 560/48; 558/418; 562/457

[56] References Cited

U.S. PATENT DOCUMENTS

| | | | |
|---|---|---|---|
| 3,219,704 | 11/1965 | Wilder et al. | 260/576 |
| 3,272,865 | 9/1966 | Barker | 260/581 |
| 3,931,298 | 1/1976 | Wollensak | 260/581 |
| 4,431,841 | 2/1984 | Malz et al. | 564/398 |

FOREIGN PATENT DOCUMENTS 46-23052 7/1971 Japan .
46-23053 7/1971 Japan .
14738 4/1974 Japan .
49-924 5/1974 Japan .
5489 2/1977 Japan .
58-648 4/1982 Japan .

OTHER PUBLICATIONS

Methoden der Organischen Chemie, vol. XI/1, pp. 112–122.

*Primary Examiner*—Richard L. Raymond
*Assistant Examiner*—John A. Sopp
*Attorney, Agent, or Firm*—Fisher, Christen & Sabol

[57] ABSTRACT

Diphenylamines or N,N'-diphenyl-phenylenediamines can be obtained by heat-reacting an aniline or a phenylenediamine with preferably an excess of a phenol in an amount of 4 to 20 moles per mole of the aniline or phenylenediamine in the presence of a hydrogen transfer catalyst and a cyclohexanone corresponding to said phenol.

The excess phenol used in the reaction undergoes reduction in the reaction system to form a cyclohexanone, which in turn reacts with the aniline or phenylenediamine to form a Schiff base and is thus consumed. The Schiff base forms the intended product by means of a dehydrogenation reaction, and the hydrogen evolved at this time reduces the phenol to form a cyclohexanone.

The phenol present in excess thus becomes in the system a solvent, a starting material for the cyclohexanone, and an acceptor of the hydrogen that forms as a by-product at the time of formation of the intended product. Hence, it becomes possible to obtain the intended product at a high selectivity from the anilines and phenylenediamines.

The process of this invention is an advantageous process for the industrial production of especially the nuclearly substituted diphenylamines.

17 Claims, No Drawings

PROCESS FOR PRODUCING DIPHENYLAMINES OR N,N'-DIPHENYL-PHENYLENEDIAMINES

This is a continuation of application Ser. No. 903,427, filed on Sept. 4, 1986, which is a divisional of application Ser. No. 710,662, filed on Mar. 12, 1985.

BACKGROUND OF THE INVENTION

1. Field of the Invention

This invention relates to a process for producing the diphenylamines or N,N'-diphenyl-phenylenediamines. More specifically, this invention relates to a process for producing the diphenylamines or N,N'-diphenyl-phenylenediamines by heat-reacting an aniline or a phenylenediamine with a phenol in the presence of a hydrogen transfer catalyst and a cyclohexanone corresponding to said phenol, using the phenol in an excessive amount to the aniline or phenylenediamine.

2. Background Art

In the past, the known processes for producing the diphenylamines include that in which the diphenylamines are produced by a deammoniation reaction from such amines as aniline or that in which the diphenylamines are produced by either a dehydration or dehydrobromination reaction from amines and phenols or bromobenzene. As specific suggestions, there has been proposed a process for producing a diphenylamine from a phenol and aniline using gamma-alumina as catalyst (Japanese Patent Publication No. 14738/1974), and a process involving acetylation of 2-methyl-4-methoxyaniline, reacting the resultant product with bromobenzene, and thereafter hydrolyzing the resulting 2-methyl-4-methoxy-N-acetyldiphenylamine to give 2-methyl-4-methoxydiphenylamine (Japanese Patent Publication No. 5489/1977).

On the other hand, as processes for producing the N-alkyldiphenylamines, known are such processes as that wherein a diphenylamine is reacted with an alkyl halide, dialkyl sulfate or trialkyl phosphate, and that in which a hydrochloride of diphenylamine and alcohol are reacted. And as the process for producing the N,N'-diphenyl-phenylenediamines, known is that in which phenylenediamine, dihydroxybenzene or disulfoxybenzene, and aniline or a salt thereof are reacted.

All of the foregoing processes are however extremely unsatisfactory for use as industrial processes.

As a process differing from the foregoing processes, also known is a process which involves reacting an amine with a Schiff base. Specifically, there has been suggested a process involving reaction N-cyclohexylideneaniline in the vapor phase with an oxygen-containing gas in the presence of an oxidizing catalyst such as silica (Japanese Laid-Open Patent Publication No. 49,924/1974), or a process which comprises heat-reacting N-methylaniline and cyclohexanone in the presence of a palladium catalyst and thereafter submitting the resulting Schiff base to a dehydrogenation reaction to give N-methyldiphenylamine (U.S. Pat. No. 3,219,704). The dehydrogenation reaction of these processes are however carried out in the absence of a hydrogen acceptor, with the consequence that the yields are unsatisfactory low values despite the fact that the N-methylaniline and cyclohexanone are used in nearly equivalent ratio.

Further, there has also been suggested a process which uses a styrene as the hydrogen acceptor in producing diphenylamines via a Schiff base such as N-cyclohexylideneaniline by reacting an amine with a cyclohexanone in the presence of a hydrogenating catalyst such as a palladium catalyst (Japanese Laid-Open Patent Publication No. 58,648/1982).

Specifically, this process is a process for obtaining 4-aminodiphenylamine from p-phenylenediamine. This process is on the whole satisfactory as regards its reaction rate and selectivity. However, for obtaining the intended product this process requires the use of an aniline and a substantially equivalent amount of a cyclohexanone. And the not readily available cyclohexanones must be synthesized from the phenols in a separate step. Further, the styrenes are only utilized as a hydrogen acceptor. This process thus cannot be regarded as being an industrially satisfactory process for producing the diphenylamines.

If a more detailed description is made, in the process of the foregoing Japanese Laid-Open Patent Publication No. 58,648/1982 the styrene added as a hydrogen acceptor becomes catalytically hydrogenated to become an entirely different compound that cannot be incorporated into the reaction system of this process, and it thus cannot be recycled for reuse. Hence, unless there can be conceived an effective use for this compound, the process becomes extremely costly when applied industrially. Further, since the styrene, as described above, becomes catalytically hydrogenated to become an entirely different compound that cannot be incorporated into the reaction system of this process, the proportion in which the amines and cyclohexanones used must be brought as close as possible to the equivalent ratio. Otherwise, a separate step for separating and purifying the excess amines and/or cyclohexanones will be required, or a loss in the amines or cyclohexanones will be brought about.

BROAD DESCRIPTION OF THE INVENTION

The anilines, as used herein, are compounds of the formula:

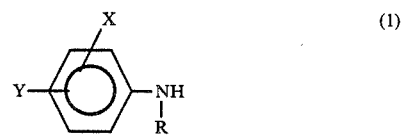

wherein R is hydrogen or a lower alkyl group, and X and Y are hydrogen, fluorine, or an alkyl, alkoxy, carboxyl, carboxyl esters, cyano, hydroxyl or benzyl group, which substituents may be the same or different. And the phenylenediamines, as used herein, are compounds of the formula:

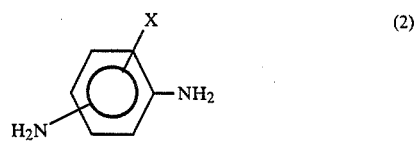

wherein X is hydrogen or a lower alkyl group. On the other hand, the phenols corresponding to the cyclohexanones are compounds of the formula:

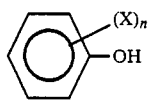

(3)

wherein X is a lower alkyl group or a lower alkoxy group, and n is an integer from 0 to 2.

An object of the present invention is therefore to improve on these defects of the conventional processes.

The present inventors have engaged in extensive investigations with the view of achieving this object. These investigations led to the discovery that when an aniline of the aforesaid formula (1) or a phenyldiamine of the formula (2) (for brevity, these are referred to hereinafter as amines) is heat-reacted in the presence of a hydrogen transfer catalyst and an excess of a phenol, with a cyclohexanone corresponding to the phenol, the formation of a Schiff base as a result of a condensation reaction between the amine and the cyclohexanone takes place, as well as its dehydrogenation reaction is set up, and simultaneously there is formed afresh in the same reaction system by the reduction of phenol a cyclohexanone in an amount corresponding to that consumed in the condensation reaction. It was hence found that the reaction proceeds readily simply by causing the presence of a catalytic amount of the cyclohexanone in the early stage of the reaction, and moreover that even though the amine has a nuclearly substituted group the intended product can be obtained at a high selectivity by carrying out the reaction in the presence of an excess of the phenol.

There is thus provided in accordance with this invention a process for producing diphenylamines either by heat-reacting an amine and an excess of a phenol in the presence of a hydrogen transfer catalyst and a catalytic amount of a cyclohexanone corresponding to the phenol of the aforesaid formula (3) used in the reaction; or by a procedure in which the cyclohexanone is not caused to be present in the reaction system from the outset but by heat-reacting a phenol with an amine while converting a part of the excessively charged phenol under hydrogen pressue to its corresponding cyclohexanone.

The process of this invention not only gives satisfactory results in respect of the reaction rate and the selectivity for the intended product, but also since the phenols are hydrogen acceptors as well as the supply source of the cyclohexanones that are formed as a result of their being hydrogen acceptors, there is the advantage that the cyclohexanone-containing phenols that are separated at the time of recovery of the intended diphenylamines can be directly recycled and reused in the reaction system in their as-mixed state. Further, in the process of this invention hydrogen is formed by dehydrogenation of the Schiff base, the intermediate product, formed by the reaction between the amines and the cyclohexanones, and the so formed hydrogen is utilized in the same reaction system in reducing the phenols, i.e., the formation of the cyclohexanones. The process is thus extremely efficient. Again, in the case of some types of the nuclearly substituted diphenylamines difficulty is experienced in producing these by a single-stage reaction, but in accordance with the process of this invention the synthesis of these compounds by a single-stage reaction is possible. And even in those cases where the suitable corresponding cyclohexanones are not easily available, there is the advantage that in accordance with the process of this invention the reaction can be carried out using in place of such cyclohexanones an excess of the phenols and carrying out the reaction while converting a part of the phenols to cyclohexanones under hydrogen pressure.

As the phenols to be used as the starting material in the process of this invention, included are, for example, phenol; the alkyl phenols such as methylphenol, ethylphenol, isopropylphenol, butylphenol, 2,4-dimethylphenol, 2,4,6-trimethylphenol and 2,6-di-t-butyl-4-methylphenol; and the alkoxy phenols such as 3-methoxyphenol and 4-methoxyphenol, especially preferred being phenol.

As to the amount of the phenols to be used, while the reaction proceeds with an amount equivalent to the amines when the cyclohexanones are used from the outset, there is a tendency to a decline in the selectivity. Hence, the phenols must be used in excess, i.e., at least 2 moles, and preferably from 4 to 20 moles, per mole of the amines.

As the aniline of the aforesaid formula (1), there can be named, for example, aniline, N-alkylanilines and the nuclearly substituted products of these anilines. All of these can give the corresponding intended product at high selectivities. From the standpoint of the demand for the product, it is however advantageous commercially to apply the process of this invention to the nuclearly substituted products. Examples of the nuclearly substituted products include such alkyl anilines as 2-methylaniline; such dialkyl anilines as 3,4-dimethylaniline, such alkoxy anilines as 3-methoxyaniline; such alkylalkoxy anilines as 2-methyl-4-methoxyaniline; o-aminobenzoic acid and esters thereof; o-aminobenzonitrile; 4-benzylaniline; aminophenol; and the fluoro alkyl anilines such as 2-fluoro-5-methylaniline. And as the N-alkyl group of the N-alkylanilines, included are say methyl, ethyl and propyl.

On the other hand, as the phenylenediamines of the aforesaid formula (2), there can be named, for example, p-phenylenediamine, m-phenylene diamine, o-phenylenediamine and toluenediamine.

Usable as the cyclohexanones are those corresponding to the phenols mentioned hereinbefore. The use of the cyclohexanones in a catalytic amount will do, and usually, if it is used in an amount of at least about 0.03 mole per mole of the amines, no special problems will arise. When the amine is an aniline of formula (1), it is preferably used in an amount of 0.05 to 0.40 mole per mole of the amine. On the other hand, when the amine is a phenylenediamine of formula (2), it is preferably used in an amount of at least 0.5 mole per mole of the amine. When the amount used is less than these amounts, the reaction rate is reduced, whereas when the amount exceeds these amounts, this also is undesirable, since a decline takes place in the yields of the intended diphenylamines and N,N'-diphenylene-diamines.

On the other hand, when the cyclohexanones are not used from the outset of the reaction, the following procedure will do. To wit, the heat-reaction is carried out after introducing and sealing in the reactor hydrogen in an amount corresponding to that which forms the cyclohexanone in a proper amount such as indicated hereinabove, i.e., on the basis of the phenols, at least about 0.06 mole (preferably from 0.10 to 0.80 mole when the amine is an aniline and at least 0.6 mole when the amine is a phenylenediamine).

The catalyst used in the process of this invention must be one having the function of catalyzing both the dehydrogenation and reduction reactions. Usually, a suitable hydrogenating catalyst is also suitably used with the dehydrogenation reaction. Specific examples of such a catalyst are the supported Raney nickel, reduced nickel or nickel catalysts, supported Raney cobalt, reduced cobalt or cobalt catalysts, supported Raney copper, reduced copper or copper catalysts, catalysts of the noble metals of group VIII of the periodic table or catalysts obtained by supporting these metals on a carrier material such as carbon, alumina or barium carbonate, rhenium catalysts such as rhenium-carbon, and the copper-chromate catalysts. Of these catalysts, preferred is palladium, and especially preferred are such supported catalysts of palladium as palladium-carbon, palladium-alumina and palladium-magnesium oxide. These catalysts are used, based on the amines, in an amount calculated as metal atoms, of usually 0.001 to 0.2 gram-atom, preferably 0.004 to 0.1 gram-atom.

A reaction temperature of 130° to 350° C. is usually employed. When the amine is aniline or its nuclearly substituted product, a temperature in the range of 170° to 280° C. is preferably chosen, whereas when the amine is an N-alkylaniline or its nuclearly substituted product, a temperature in the range of 130° to 200° C. is preferably chosen.

The intended diphenylamines can be obtained by treating the reaction-completed mixture in customary manner, for example, distillation, crystallization or extraction. At this time, as a preferred mode of practicing the invention process, the cyclohexanone-containing excess phenol obtained after completion of the reaction is recycled in its as-obtained state for reuse in the second and subsequent reactions. Specifically, the liquid obtained after completion of the reaction is filtered to separate the catalyst, which can be reused. The filtrate is then concentrated, and the cyclohexanone-containing phenol is recovered, followed by returning this fraction to the reaction system in its as-mixed state. The diphenylamine remaining in the kettle is then purified and separated by say distillation, crystallization, etc.

The industrially valuable and expensive diphenylamines or N,N'-diphenyl-phenylenediamines can thus be easily obtained from the amines in accordance with the process of this invention. For example, 2-methyl-4-methoxy-diphenylamine could only be obtained by roundabout methods such as the process disclosed in Japanese Patent Publication No. 5489/1977, which is carried out in accordance with the following reaction scheme:

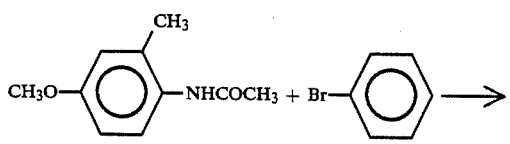

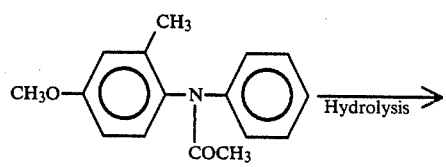

-continued

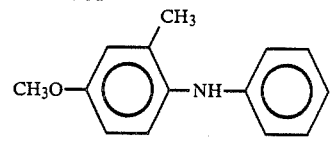

or the process disclosed in Japanese Laid-Open Publication No. 136,252/1980, which is carried out in accordance with the following reaction scheme:

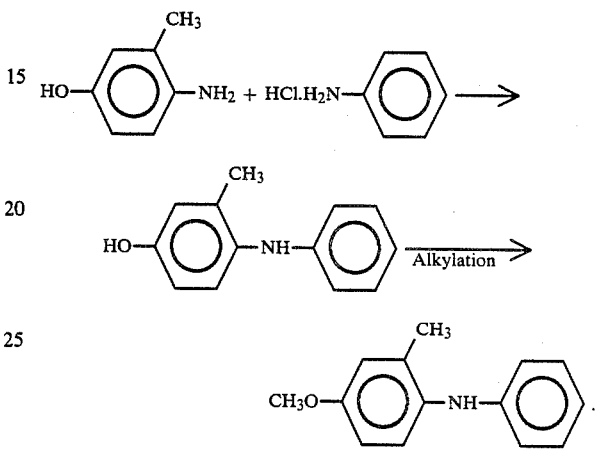

It is now however possible by the utilization of the process of this invention to obtain 2-methyl-4-methoxydiphenylamine from 2-methyl-4-methoxyaniline and phenol in a single stage and moreover in a high yield. The process of this invention can therefore be regarded as being an extremely advantageous process for say the industrial production of 2-alkyl-4-alkoxydiphenylamines.

The process of this invention is an especially advantageous method for producing industrially the nuclearly substituted diphenylamines from the nuclearly substituted products of aniline of the formula (1) that have been substituted by the alkyl groups and/or alkoxy groups and/or fluorine.

The diphenylamines and N,N'-diphenyl-phenylenediamines are compounds that are useful as intermediates for the production of dyestuffs, agricultural chemicals, medicines, rubber compounding agents, etc. The nuclearly substituted diphenylamines, for example, 2-methyl-4-alkoxydiphenylamine and 2-methyl-4-alkoxy-2',4'-dimethyl-diphenylamine, as starting materials for dyes for use with the fluoran-type pressure-sensitive or heat-sensitive recording papers, and 2-chloro-5-methyldiphenylamine, as a starting material of agricultural chemicals, are especially expensive and valuable compounds.

DETAILED DESCRIPTION OF THE INVENTION

The following examples will serve to illustrate the process of the present invention more specifically.

EXAMPLE 1

A 500-ml stainless steel autoclave was charged with 21.4 g (0.2 mole) of 2-methylaniline, 94.1 g (1.0 mole) of phenol, 2.0 g (0.02 mole) of cyclohexanone and 1.07 g of 5% palladium-carbon (product of Japan Englehard Ltd.). After purging the inside of the autoclave with nitrogen, the temperature was raised to 200° C., after which the reaction was carried out at this temperature for 3 hours with stirring. The temperature was then returned to room temperature, after which the reaction mixture was filtered to separate a catalyst.

A part of the filtrate was taken, and the unreacted starting materials and product were quantitatively determined by gas chromatography. The analysis showed that 0.3 g (conversion 98.6%) of unreacted 2-methylaniline remained and that 35.8 g (selectivity 99.2%) had been formed. The filtrate was then distilled to concentrate and separate, and recover 6.0 g of a fraction of phenol containing cyclohexanone. The concentration of cyclohexanone in the fraction was 2.4%, which corresponds to 91.2% of the amount of cyclohexanone charged. The concentrated liquid obtained after separation of the phenol was again distilled under reduced pressure to give 34.8 g (yield 95%) of a fraction boiling at 173° to 179° C. at a reduced pressure of 20 mmHg.

This was followed by carrying out the reaction in like manner but adding only 20.0 g of phenol to the aforesaid recovered catalyst and recovered phenol fraction containing cyclohexanone and without the addition afresh of cyclohexanone. This reaction gave 2-methyl-diphenylamine at a conversion of 97.7% and a selectivity of 99.3%. The cyclohexanone concentration in the phenol fraction was 2.2%.

EXAMPLE 2

A 500-ml stainless steel autoclave was charged with 64.2 g (0.6 mole) of 2-methylaniline, 56.5 g (0.6 mole) of phenol, 6.0 g (0.06 mole) of cyclohexanone and 3.2 g of 5% palladium-carbon. After the inside of the autoclave was purged with nitrogen, the temperature was raised to 200° C., and the reaction was carried out for 7 hours at this temperature with stirring. After completion of the reaction, the reaction product was treated as in Example 1 and then analyzed in the same manner. It was found as a result of the analysis that 1.2 g (conversion 98.1%) of unreacted 2-methylaniline remained and that 98.5 g (selectivity 91.3%) of 2-methyldiphenylamine had been formed. These results show that the use of phenol in the reaction in an equivalent amount was a disadvantage.

EXAMPLE 3

The reaction was carried out in the same manner as in Example 1 but using 5% palladium-magnesium oxide instead of 5% palladium-carbon, after which the reaction product was treated in like manner.

As a result of the foregoing experiment, 1.2 g (conversion 94.4%) of unreacted 2-methylaniline remained and 33.1 g (selectivity 95.8%) of 2-methyl-diphenylamine was formed.

EXAMPLE 4

A 500-ml autoclave of the same type as used in Example 1 was employed, and this autoclave was charged with the same charge materials as in Example 1, except that the initially charged cyclohexanone was absent. After purging the inside of the autoclave with nitrogen, a pressure of 5 kg/cm$^2$.G was built up with hydrogen. The amount of this hydrogen corresponds to about 0.3 mole per mole of the 2-methylaniline (i.e. 0.3 mole as the amount of cyclohexanone formed from the phenol used in the reaction). The reaction was carried out in the same manner as in Example 1 followed by the same treatment.

As a result of having carried out the experiment in this manner, there was formed 2-methyl-diphenylamine at a selectivity of 99.0%. And cyclohexane was present in the recovered phenol fraction, and its concentration was 3.3%.

EXAMPLE 5

Example 1 was repeated but using 3,4-dimethoxyaniline instead of 2-methylaniline. Unreacted 3,4-dimethoxyaniline was not noted, and 3,4-dimethoxy-diphenylamine was obtained at a selectivity of 97.0%.

EXAMPLE 6

The experiment was carried out as in Example 1 but using 2-methyl-4-methoxyaniline instead of 2-methylaniline. At a conversion of 98.0%, 2-methyl-4-methoxy-diphenylamine was formed at a selectivity of 98.0%.

The filtrate resulting after separation of the catalyst was concentrated to separate and recover a phenol fraction, after which the concentrated liquid was distilled under reduced pressure to give 39.3 g (yield 94.0%) of a fraction boiling a 192° to 198° C.

EXAMPLE 7

Example 1 was repeated but using 2,4-dimethylphenol instead of phenol. At a conversion of 98.5%, 2-methyl-4-methoxy-2',4'-dimethyl-diphenylamine was formed at a selectivity of 93.0%.

EXAMPLE 8

The experiment was conducted as in Example 1 but using 2-fluoro-5-methylaniline instead of 2-methylaniline, whereupon a virtual completion of the reaction was achieved, and 2-fluoro-5-methyl-diphenylamine was obtained at a selectivity of 95.5%.

EXAMPLE 9

A 500-ml stainless steel autoclave was charged with 24.2 g (0.2 mole) of 2-methyl-N-methylaniline, 94.1 g (1.0 mole) of phenol, 2.0 g (0.02 mole) of cyclohexanone and 1.07 g of 5% palladium-carbon. After purging the inside of the autoclave with nitrogen, the temperature was raised to 150° C. The reaction was then carried out for 8 hours at this temperature with stirring, after which the temperature was cooled to room temperature, and the reaction mixture was filtered to separate a catalyst.

A part of the filtrate was taken, and the unreacted starting materials and the product were quantitatively determined by gas chromatography. The analysis showed that 0.8 g (conversion 96.7%) of 2-methyl-N-methylaniline remained and 33.8 g (selectivity 88.7%) of 2-methyl-N-methyl-diphenylaniline had been formed. The filtrate was distilled to concentrate and separate, and recover 75.8 g of a fraction of phenol containing cyclohexanone. The concentration of cyclohexanone in the fraction was 2.2%, and this corresponds to 83.4% of the amount of cyclohexanone charged.

This was followed by carrying out the reaction in like manner but adding only 20.0 g of phenol to the aforesaid recovered catalyst and recovered phenol fraction containing cyclohexanone and without the addition afresh of cyclohexanone. This reaction gave 2-methyl-N-methyl-diphenylamine at a conversion of 96.0% and a selectivity of 90.0%. The cyclohexanone concentration in the recovered phenol fraction was 2.4%.

EXAMPLE 10

Example 9 was repeated but using 2-methyl-4-methoxy-N-methylaniline instead of 2-methyl-N-methylaniline. The intended product was obtained in this case at a conversion of 97.5% and a selectivity of 89.0%.

EXAMPLE 11

A 500-ml stainless steel autoclave was charged with 21.6 g (0.2 mole) of m-phenylenediamine, 141.2 g (1.5 mole) of phenol, 9.8 g (0.1 mole) of cyclohexanone and 2.16 g of 5% palladium-carbon. After purging the inside of the autoclave with nitrogen, the temperature was raised to 200° C. After carrying out the reaction at this temperature for 12 hours with stirring, the autoclave was cooled to room temperature, and the reaction mixture was filtered to separate a catalyst.

A part of the filtrate was taken and analyzed by gas chromatography. It was found that 52.1 g (yield 91.0%) of N,N'-diphenyl-m-phenylenediamine had been formed. The filtrate was distilled to concentrate and separate, and recover 96.8 g of a phenol fraction containing cyclohexanone. The concentration of cyclohexanone therein was 8.7%, which corresponds to 85.9% of the amount of cyclohexanone charged.

This was followed by carrying out the reaction in like manner, adding 52.8 g of phenol and 0.032 g of a fresh catalyst to the aforesaid recovered catalyst and recovered cyclohexanone-containing phenol fraction but without the addition afresh of cyclohexanone. N,N'-diphenyl-m-phenylenediamine was thus obtained at a yield of 90.3%. And the concentration of cyclohexanone in the recovered phenol fraction was 9.0%.

EXAMPLE 12

Example 9 was repeated but using 3,5-dimethylphenol instead of phenol. There was thus obtained N,N'-di(3,5-dimethylphenol)-m-phenylenediamine at a yield of 89.2%. 3,5-Dimethylcyclohexanone was present in the recovered 3,5-xylenol fraction at a concentration of 8.6%.

What is claimed is:

1. Process for producing a diphenylamine which comprises heat-reacting an aniline of the formula:

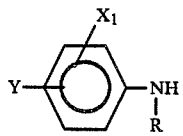

(1)

wherein
R is a member selected from the group consisting of hydrogen and a lower alkyl group, and
$X_1$ and Y are each a member selected from the group consisting of hydrogen, fluorine, an alkyl group, an alkoxy group, a carboxyl group, a carboxyl ester, a cyano group, a hydroxyl group and a benzyl group, said substituents can be the same or different, with an excess of a phenol of the formula:

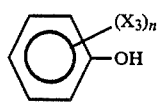

(3)

wherein
$X_3$ is a member selected from the group consisting of a lower alkyl group and a lower alkoxy group, and
n is an integer from 0 to 2,
said reaction being carried out in the presence of a catalyst system consisting of (A) a member selected from the group consisting of (1) a hydrogen transfer catalyst and (2) a hydrogen transfer catalyst supported on a carrier, and (B) a catalytic amount of a cyclohexanone corresponding to said phenol of formula (3) and said phenol is used in an excess of 4 to 20 moles per mole of said aniline.

2. The process as claimed in claim 1 which comprises separating the diphenylamine from the heat-reaction mass, and thereafter recycling the cyclohexanone-containing phenol to the reaction system for reuse.

3. The process as claimed in claim 1 wherein there is present in the reaction system at least 0.03 mole of cyclohexanone per mole of the aniline.

4. The process as claimed in claim 1 wherein there is present in the reaction system 0.05 to 0.4 mole of cyclohexanone per mole of the aniline.

5. The process as claimed in claim 1 wherein the heat-reaction temperature ranges from 130° to 350° C.

6. The process as claimed in claim 1 wherein the hydrogen transfer catalyst is palladium.

7. The process as claimed in claim 1 wherein the diphenylamine is 2-methyl-4-alkoxy-diphenylamine.

8. The process for producing diphenylamine which comprises heat-reacting in the presence of a catalyst selected from the group consisting of (1) a hydrogen transfer catalyst and (2) a hydrogen transfer catalyst supported on a carrier, an aniline of the formula:

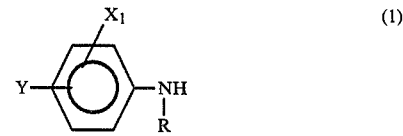

(1)

wherein
R is a member selected from the group consisting of hydrogen and a lower alkyl group, and
$X_1$ and Y are each a member selected from the group consisting of hydrogen, fluroine, an alkyl group, an alkoxy group, a carboxyl group, a carboxyl ester, a cyano group, a hydroxyl group and a benzyl group, said substituents can be the same or different, with an excess of a phenol of the formula:

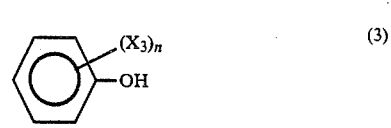

(3)

wherein
$X_3$ is a member selected from the group consisting of a lower alkyl group and a lower alkoxy group, and
n is an integer from 0 to 2,
said reaction being carried out while converting a sufficient part of said phenol under hydrogen pressure to provide a catalyst amount of its corresponding cyclohexanone, and said phenol is used in an excess of 4 to 20 moles per mole of said aniline.

9. The process as claimed in claim 8 which comprises separating the diphenylamine from the heat-reaction mass, and thereafter recycling the cyclohexanone-containing phenol to the reaction system for reuse.

10. The process as claimed in claim 8 wherein there is present in the reaction system at least 0.03 mole of cyclohexanone per mole of the aniline.

11. The process as claimed in claim 8 wherein there is present in the reaction system 0.05 to 0.4 mole of cyclohexanone per mole of the aniline.

12. The process as claimed in claim 8 wherein the heat-reaction temperature ranges from 130° to 350° C.

13. The process as claimed in claim 8 wherein the hydrogen transfer catalyst is palladium.

14. The process as claimed in claim 8 wherein the diphenylamine is 2-methyl-4-alkoxy-diphenylamine.

15. The process as claimed in claim 1 wherein the heat reaction temperature is from 170° to 280° C. when the aniline is aniline or a nuclearly-substituted aniline, and wherein the catalyst is supported.

16. The process as claimed in claim 1 wherein the heat reaction temperature is from 130° to 200° C. when the aniline is a N-alkylaniline or a nuclearly-substituted N-alkylaniline, and wherein the catalyst is supported.

17. Process for producing a diphenylamine from an amine and a phenol which comprises heat-reacting a reaction system at 170° to 280° C. in the presence of a platinum group hydrogen transfer catalyst supported on a carrier, said reaction system being obtained by charging into a reaction vessel an aniline of the formula:

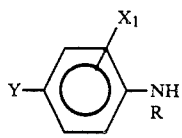

wherein
R is a member selected from the group consisting of hydrogen and a lower alkyl group, and
$X_1$ and Y are each a member selected from the group consisting of hydrogen, fluorine, an alkyl group, an alkoxy group, a carboxyl group, a carboxyl ester, a cyano group, a hydroxyl group and a benzyl group, said substituents can be the same or different, a phenol of the formula:

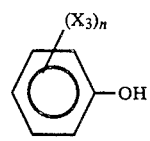

wherein
$X_3$ is a member selected from the group consisting of a lower alkyl group and a lower alkoxy group, and
n is an integer from 0 to 2, in an amount of 4 to 20 moles per mole of said aniline, and a cyclohexanone corresponding to the phenol in an amount of 0.05 to 0.4 mole per mole of said aniline, and causing a reaction of the aniline and the cyclohexanone to form a Schiff base, a dehydrogenation reaction of the resultant Schiff base to form a diphenylamine and a reaction of the phenols with a hydrogen from the dehydrogenation of the Schiff base to form a cyclohexanone to be carried in the same reaction vessel simultaneously in parallel thereby to complete the reaction into the diphenylamine.

* * * * *